United States Patent
Funderburk et al.

[11] Patent Number: 6,093,172
[45] Date of Patent: *Jul. 25, 2000

[54] INJECTOR FOR A SUBCUTANEOUS INSERTION SET

[75] Inventors: Jeffery V. Funderburk, Granada Hills; April A. Marano, Los Angeles; Jeffrey F. Field, Northridge, all of Calif.

[73] Assignee: MiniMed Inc., Sylmar, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/002,303

[22] Filed: Dec. 31, 1997

Related U.S. Application Data

[63] Continuation-in-part of application No. 08/795,968, Feb. 5, 1997, Pat. No. 5,851,197.

[51] Int. Cl.[7] .................................................. A61M 5/20
[52] U.S. Cl. ..................... 604/135; 604/131; 604/134; 604/157
[58] Field of Search .................... 604/131, 134, 604/135, 136, 137, 138, 156, 157, 187, 218, 220

[56] References Cited

U.S. PATENT DOCUMENTS

| | | |
|---|---|---|
| 4,601,708 | 7/1986 | Jordan . |
| 4,755,173 | 7/1988 | Konopka et al. . |
| 4,787,891 | 11/1988 | Levin et al. . |
| 4,988,339 | 1/1991 | Vadher . |
| 4,994,042 | 2/1991 | Vadher . |
| 5,042,977 | 8/1991 | Bechtold et al. . |
| 5,085,641 | 2/1992 | Sarnoff et al. . |
| 5,122,119 | 6/1992 | Lucas . |
| 5,137,516 | 8/1992 | Rand et al. . |
| 5,141,496 | 8/1992 | Dalto et al. . |
| 5,176,662 | 1/1993 | Bartholomew et al. . |
| 5,257,980 | 11/1993 | Van Antwerp et al. . |
| 5,300,030 | 4/1994 | Crossman et al. . |
| 5,312,354 | 5/1994 | Allen et al. . |
| 5,391,151 | 2/1995 | Wilmot . |
| 5,423,760 | 6/1995 | Yoon . |
| 5,423,770 | 6/1995 | Yoon . |
| 5,425,715 | 6/1995 | Dalling et al. . |
| 5,478,316 | 12/1995 | Bitdinger et al. . |
| 5,480,387 | 1/1996 | Gabriel et al. . |
| 5,480,388 | 1/1996 | Zadini et al. . |
| 5,584,813 | 12/1996 | Livingston et al. . |
| 5,586,553 | 12/1996 | Halili . |
| 5,591,188 | 1/1997 | Waisman . |
| 5,665,071 | 9/1997 | Wyrick ..................................... 604/134 |

FOREIGN PATENT DOCUMENTS

| | | |
|---|---|---|
| WO9521645 | 8/1995 | WIPO . |
| WO9640324 | 12/1996 | WIPO . |

*Primary Examiner*—Ronald Stright
*Assistant Examiner*—Patricia M. Bianco
*Attorney, Agent, or Firm*—MiniMed Inc.

[57] ABSTRACT

An injector is provided for automatic placement of a subcutaneous insertion set such as an infusion set or the like used for delivering a selected medication to a patient. The injector comprises a spring-loaded plunger having a head for receiving and supporting the insertion set in a position for placement of a medical insertion needle through the skin of a patient at a selected insertion site. The plunger head includes a safety lock mechanism for engaging and retaining the insertion set during spring-loaded advancement with a controlled force and speed toward the patient's skin to transcutaneously place the insertion needle. When the plunger head reaches a fully advanced position, with the insertion set placed on the patient, the insertion set is releasable from the safety lock mechanism with minimal force to permit quick and easy separation of the injector. Alternately, in some embodiments, the injector can be displaced away from the patient's skin to separate the insertion needle from the insertion set, while leaving the insertion set in place on the patient.

21 Claims, 15 Drawing Sheets

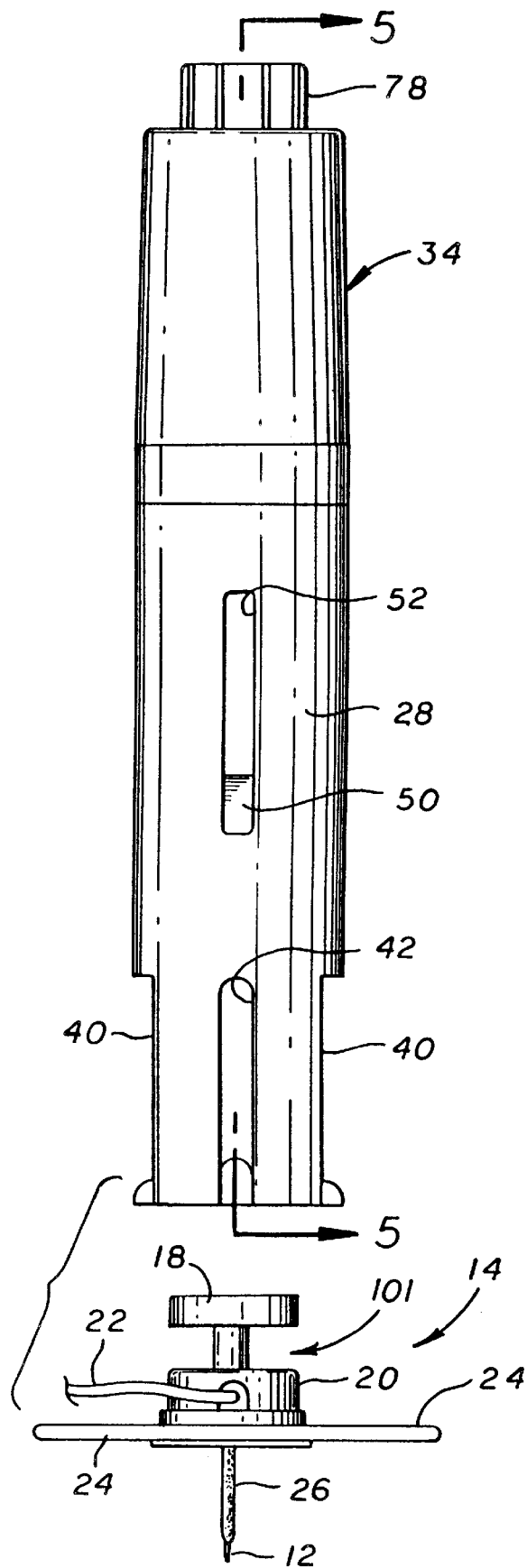

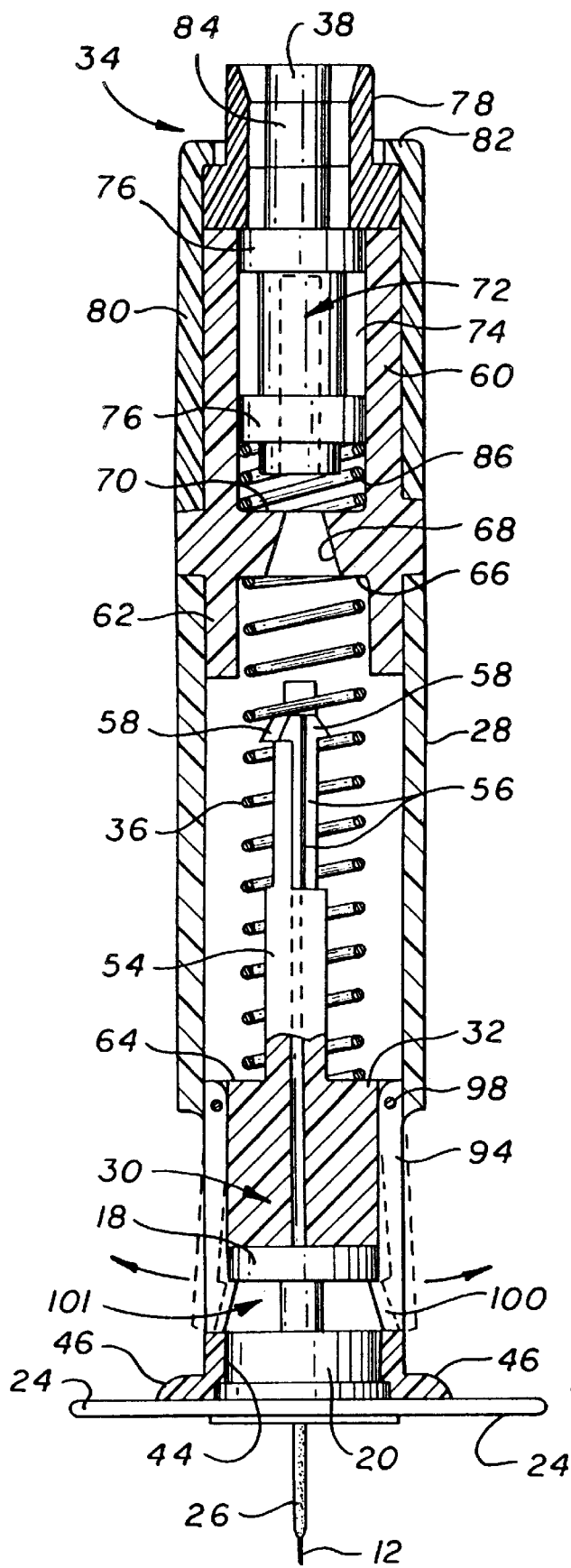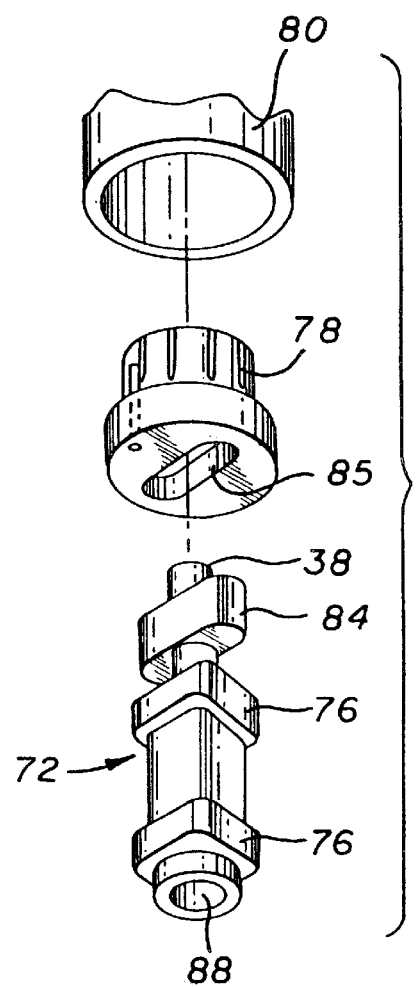
FIG. 7
FIG. 8

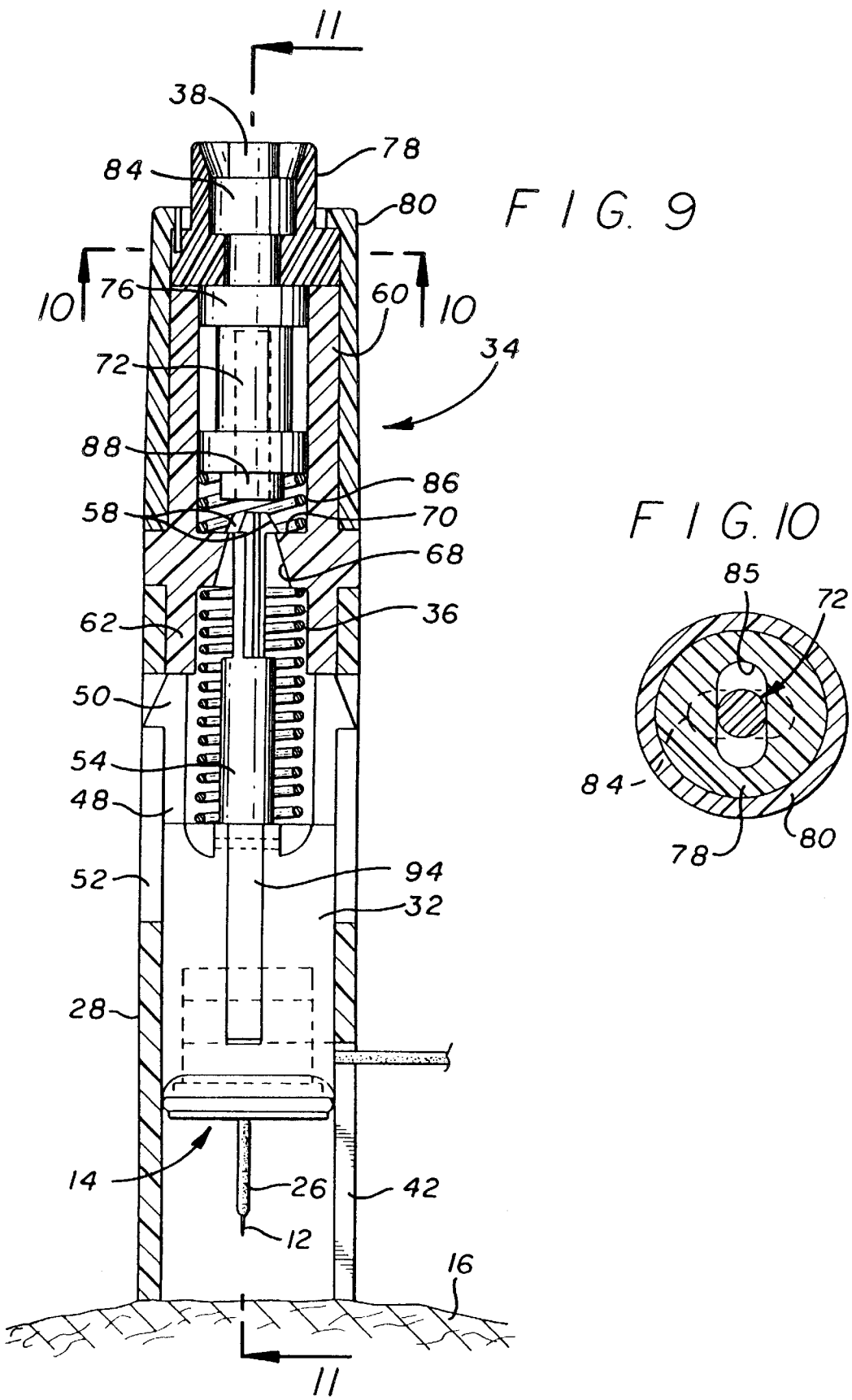

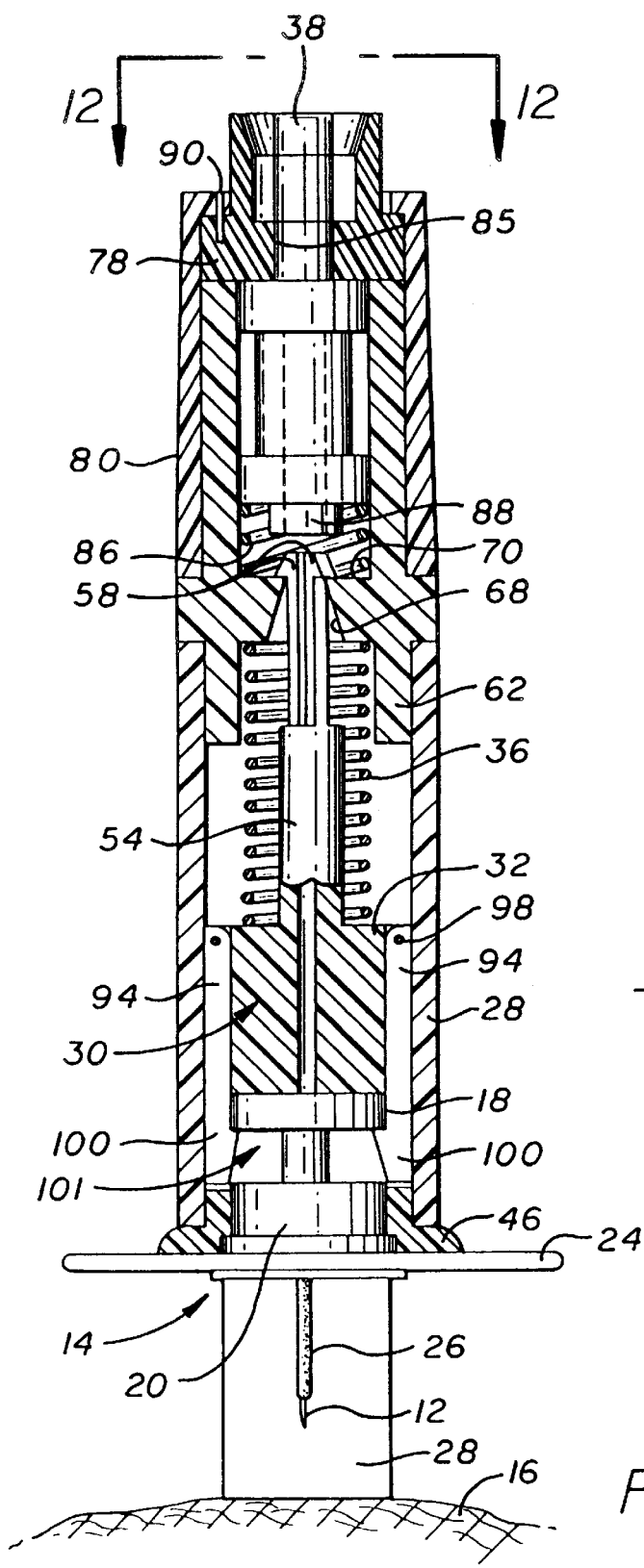
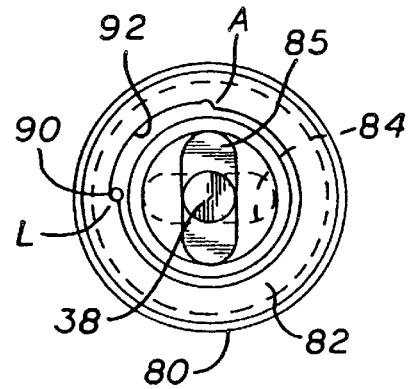
FIG. 12
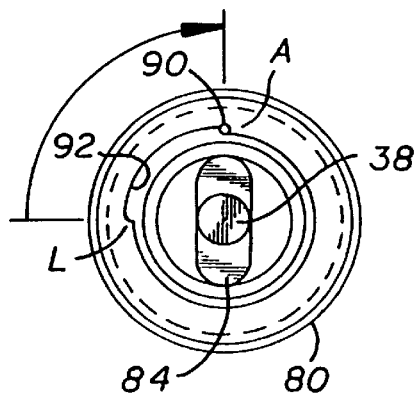
FIG. 14
FIG. 11

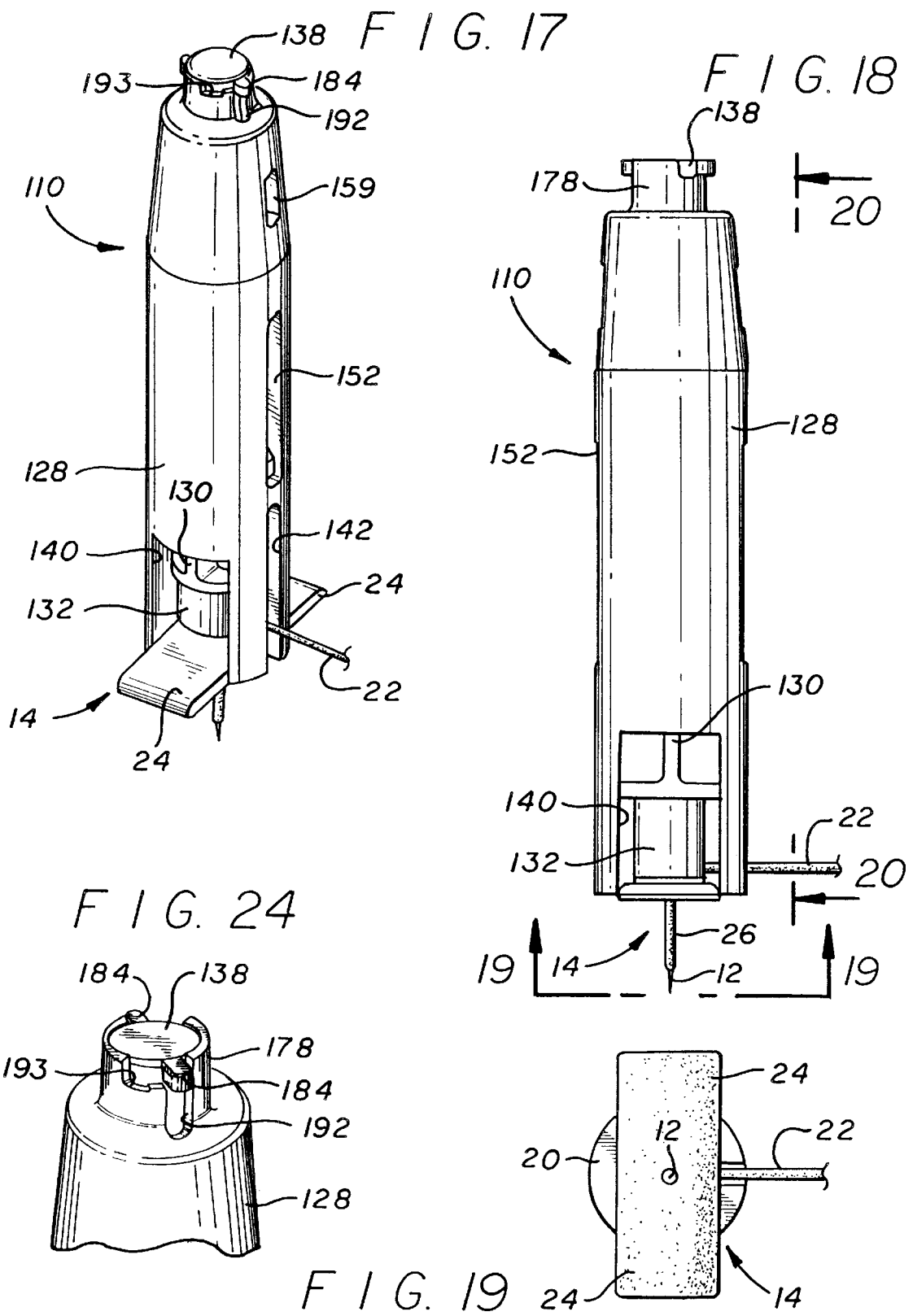

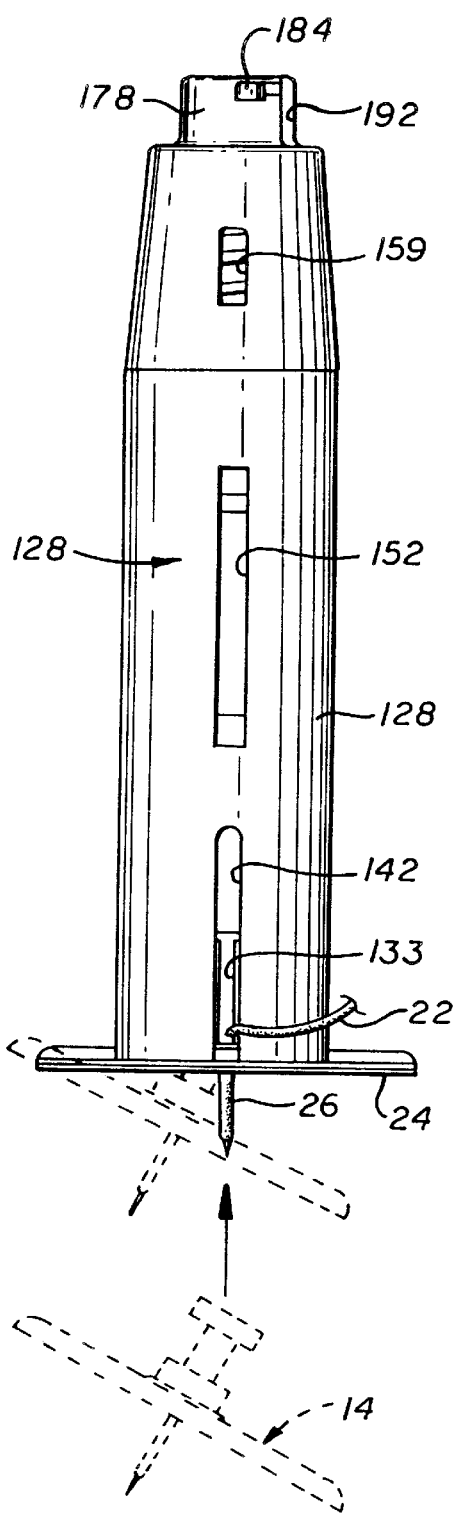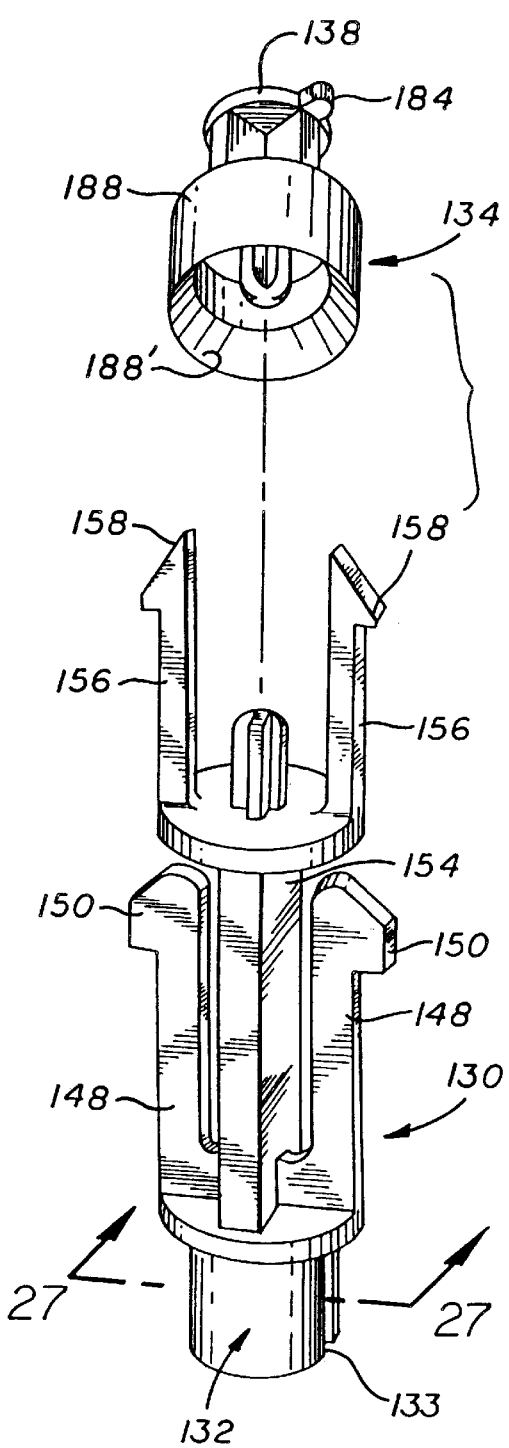

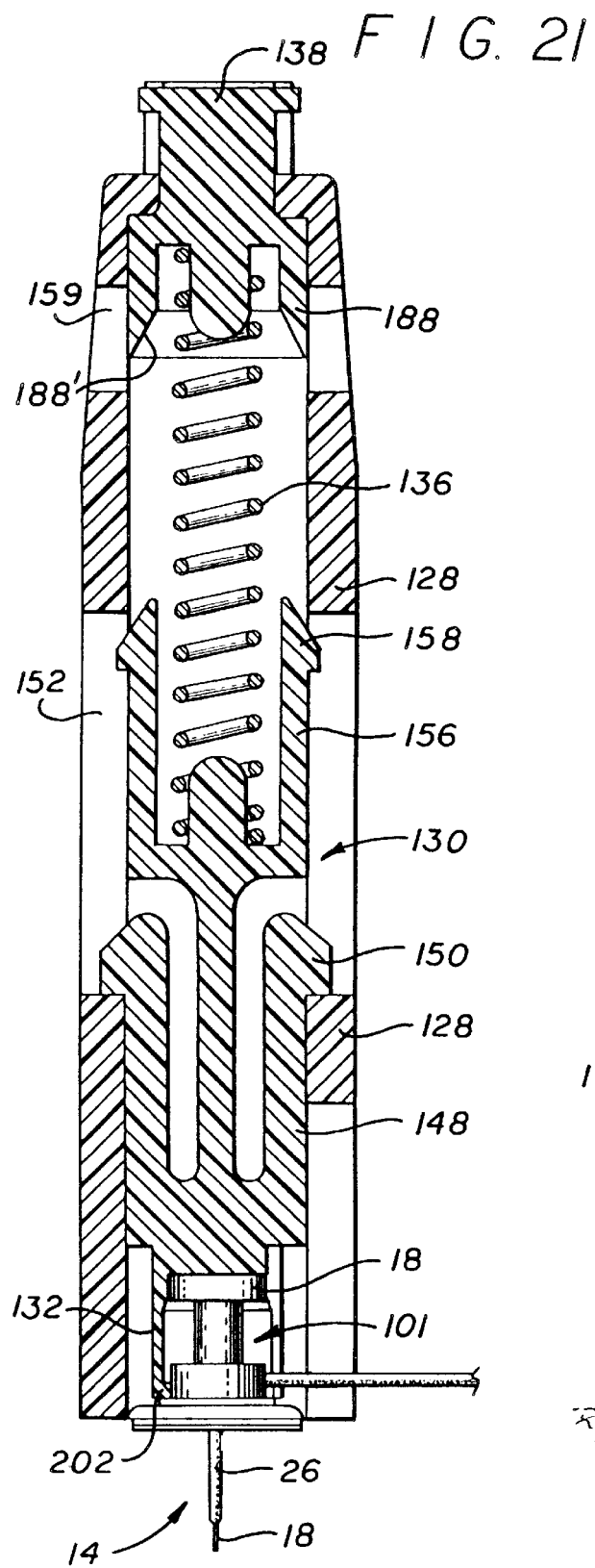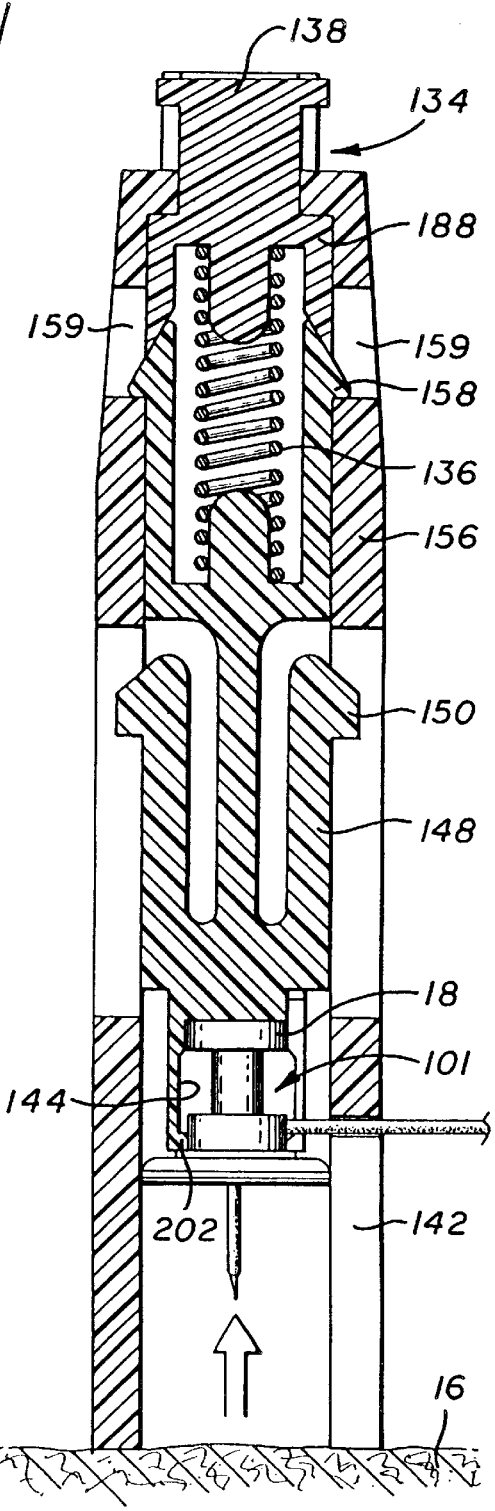

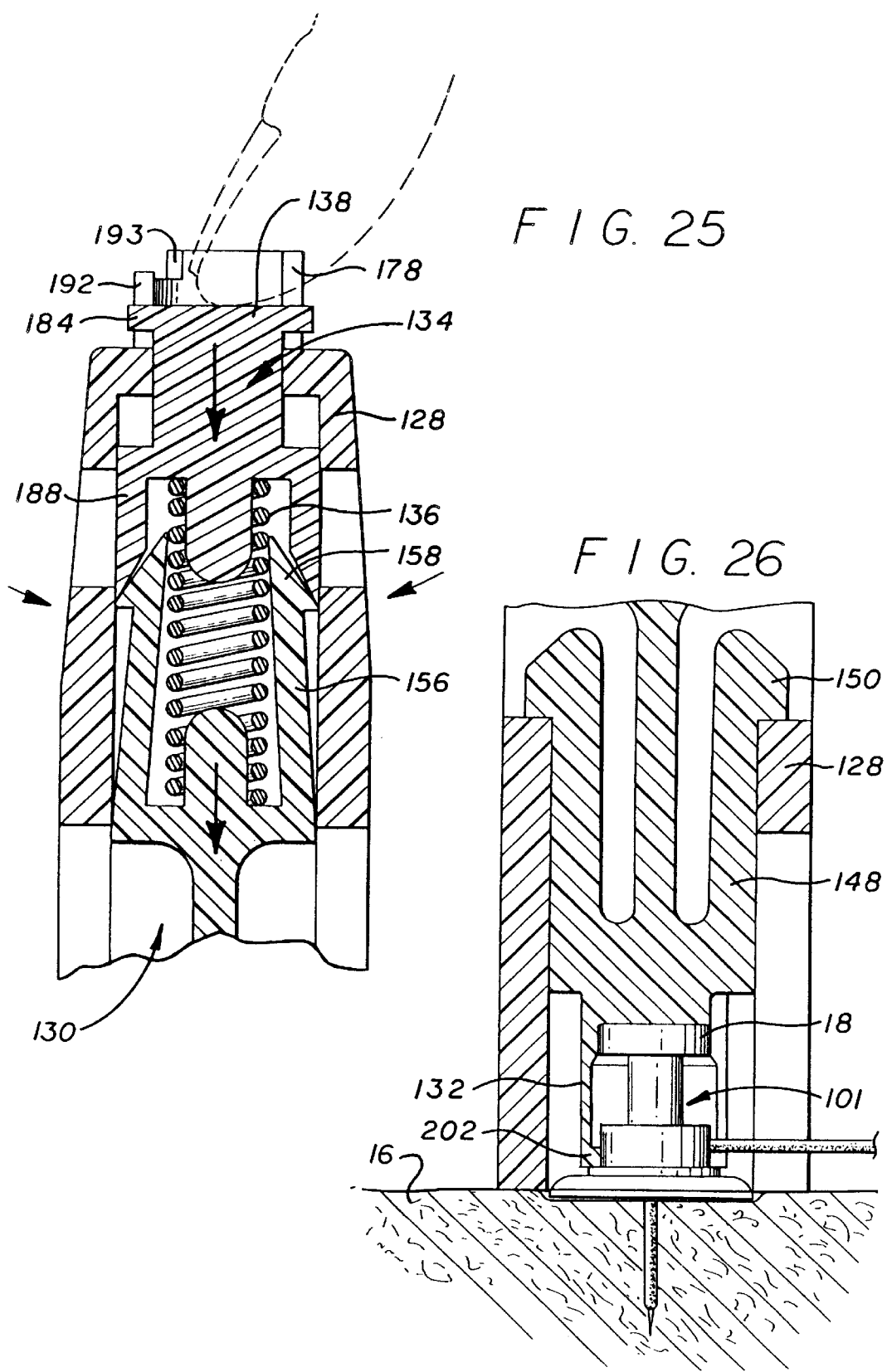

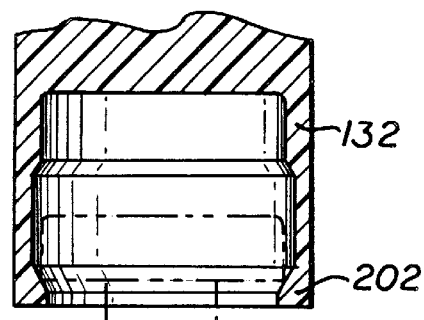
FIG. 27
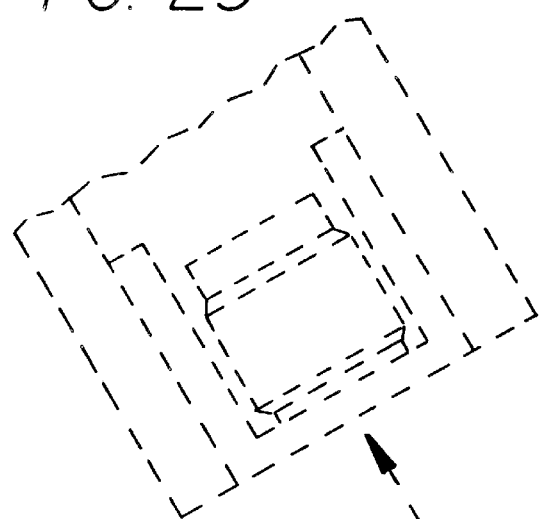
FIG. 29
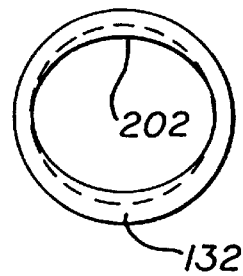
FIG. 28
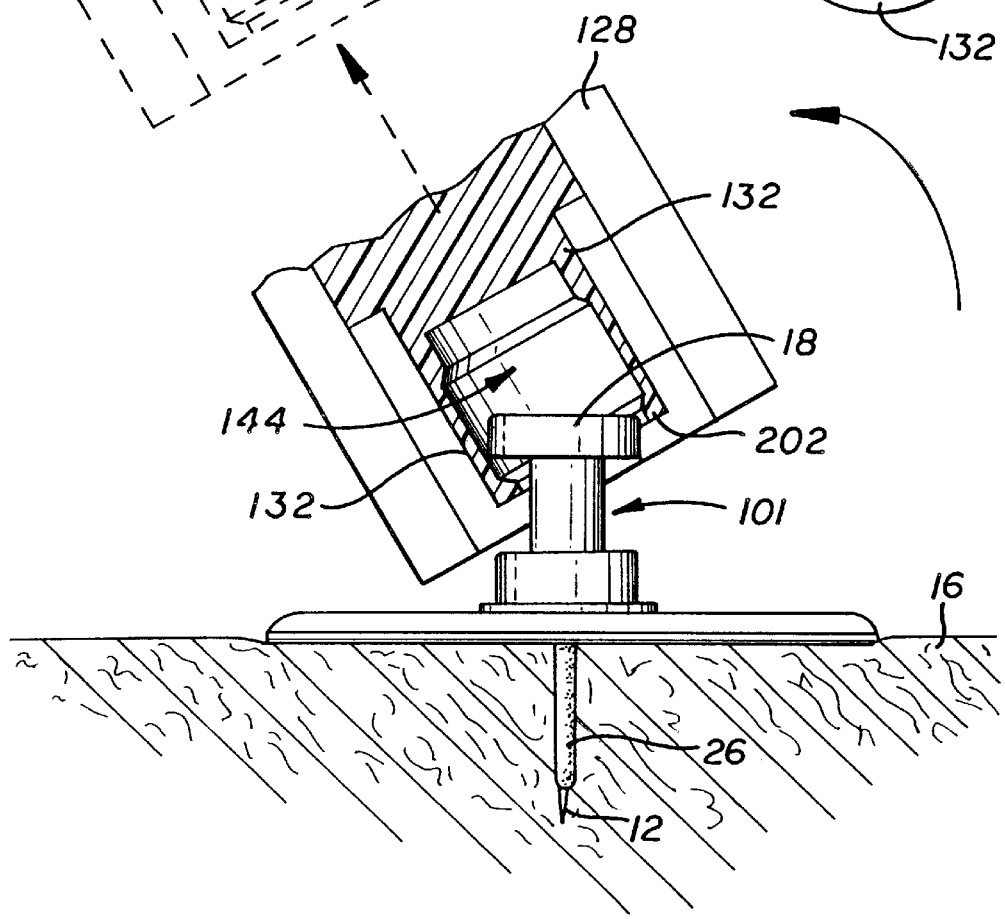

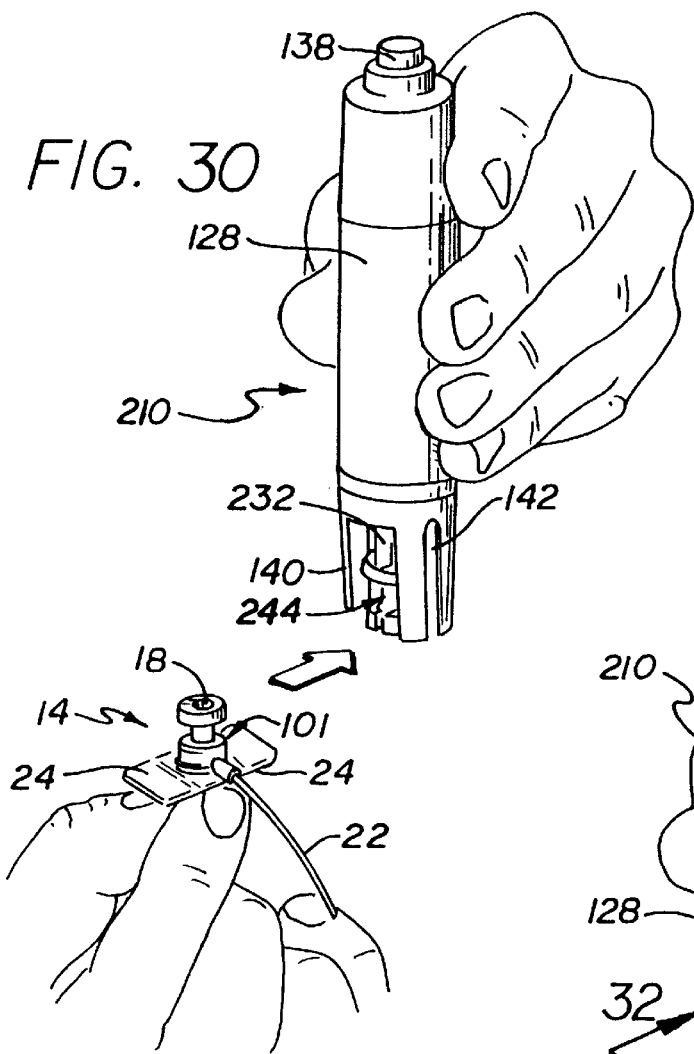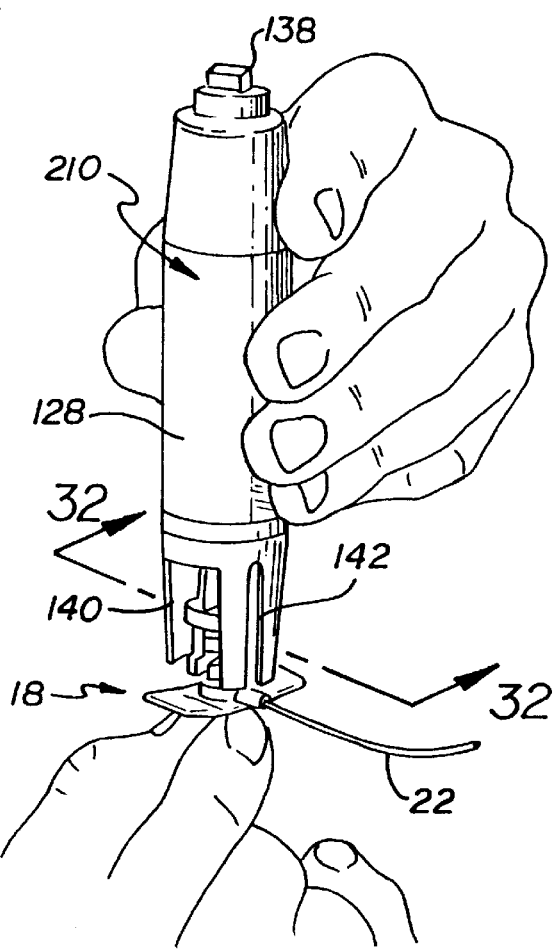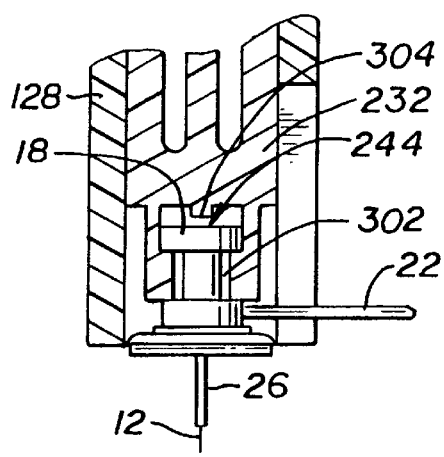

INJECTOR FOR A SUBCUTANEOUS INSERTION SET

BACKGROUND OF THE INVENTION

This application is a continuation-in-part of U.S. Ser. No. 08/795,968, filed Feb. 5, 1997 now U.S. Pat. No. 5,851,197.

This invention relates generally to an injector for automatic placement of a medical needle through the skin of a patient. More specifically, this invention relates to a compact and easily operated injector for placement of an insertion needle of a subcutaneous insertion set or the like through the skin of a patient with a controlled force and insertion speed, and particularly wherein the injector is adapted for use by the patient.

Medical needles are widely used in the course of patient care and treatment, particularly with respect to the delivery of selected medications to a patient. In one common form, hollow hypodermic needles are employed for transcutaneous delivery of a selected medication from a syringe or the like. In another common form, insertion needles are employed for transcutaneous placement of a soft and relatively flexible tubular cannula, followed by insertion needle removal and subsequent infusion of medical fluid to the patient through the cannula. More recently, insertion needles have also been used for transcutaneously placing other medical devices such as a subcutaneous sensor for monitoring specified patient parameters, such as blood glucose level.

In certain medical treatment regimens, it may be necessary or desirable for the patient to transcutaneously place the medical needle. For example, diabetic patients frequently self-administer insulin injections or periodically place a subcutaneous insertion set with a cannula for subsequent programmable delivery of insulin by means of a medication infusion pump of the general type described in U.S. Pat. No. 4,685,903. Such subcutaneous insertion sets are disclosed, for example, in U.S. Pat. Nos. 4,755,173; 5,176,662; and 5,257,980 which are incorporated by reference herein. Diabetic patients may also use a subcutaneous insertion set to periodically place a transcutaneous glucose sensor wherein such sensor insertion sets are disclosed, for example, In U.S. Pat. Nos. 5,390,671; 5,568,806; 5,586,553, which are also incorporated by reference herein.

Some patients are reluctant or hesitant to pierce their own skin with a medical needle, and thus encounter difficulties in correct needle placement for proper administration of the medication. Such difficulties can be attributable to insufficient manual dexterity or skill to achieve proper needle placement or alternately to anxiety associated with anticipated discomfort as the needle pierces the skin. This problem can be especially significant with medications delivered via a subcutaneous insertion set, since incorrect placement can cause kinking of the cannula and resultant obstruction of medication flow to the patient. Cannula kinking can be due to insertion set placement at an incorrect angle relative to the patient's skin, and/or needle placement with an incorrect force and speed of insertion.

The present invention relates to an automatic injector, particularly for use with a subcutaneous insertion set, for quickly and easily placing an insertion needle through the skin of a patient at the correct insertion angle, and with a speed and force of insertion which minimizes patient discomfort.

SUMMARY OF THE INVENTION

In accordance with the invention, an injector is provided for quick and easy transcutaneous placement of a medical needle through the skin of a patient, particularly such as an insertion needle of a subcutaneous insertion set. The injector is designed to place the needle through the skin at a selected insertion angle and with a controlled force and speed of insertion, to ensure proper needle placement with minimal patient discomfort. The injector is particularly designed to meet these objectives, while safeguarding against undesired projection of the medical needle through free space, in the event that the injector is actuated in spaced relation to the patient's skin.

The injector comprises a spring-loaded plunger having a head for receiving and supporting an insertion set in a position with an insertion needle projecting outwardly for transcutaneous placement through the skin of a patient. The plunger is designed for retraction and retention within a barrel to a cocked position with a drive spring compressed in a manner applying a predetermined spring force to the plunger head. A front or nose end of the injector barrel is designed for pressed placement against the skin of a patient, at a selected needle insertion site, and in an orientation with the needle disposed at a correct or desired insertion angle. A trigger member is operable to release the plunger and thereby permit the drive spring to carry the insertion set toward the patient's skin with a controlled force and speed, resulting in proper transcutaneous placement of the insertion needle with minimal patient discomfort.

The plunger head includes a safety lock mechanism to retain the insertion set against projection from the injector barrel. In one preferred form, the safety lock mechanism comprises at least one and preferably a pair of safety lock arms for engaging and retaining the insertion set when the plunger is retracted from a fully advanced position. Each safety lock arm includes a cam lobe for engaging an appropriately shaped recess on the insertion set to prevent release thereof from the plunger head, unless and until the plunger head is returned to the fully advanced position. In such fully advanced position, the shape of the cam lobe permits quick and easy separation of the injector from the insertion set with a minimal separation force.

In operation, the safety lock arms thus prevent projection of the insertion set from the injector, in the event that the trigger member is actuated with the nose end of the barrel spaced from the skin of a patient. In that event, the plunger head is advanced with the controlled force and speed to the fully advanced position, but the insertion set is not thrown from the injector as a projectile. Instead, the insertion set travels rapidly with the plunger head to the fully advanced position, whereat the injector can be separated with minimal separation force from the insertion set.

In an alternative preferred form, the safety lock mechanism comprises a plunger head having a cylindrical shape defining a forwardly open cavity for receiving and supporting an insertion set with the insertion needle projecting outwardly. In this embodiment, the plunger head includes a radially inwardly projecting rim at a forward or nose end thereof, wherein the rim defines an oval-shaped opening. The size of the rim opening permits relatively free reception of a needle hub on the insertion set, with the insertion set oriented at an angle relative to a central axis of the plunger head and barrel. The insertion set is then reoriented to align the insertion needle coaxially with the central axis of the barrel and plunger head, so that the rim is received into a recess on the insertion set and functions to retain the infusion set against undesired release from the injector during spring-driven placement of the needle. After needle placement, the injector is released from the insertion set with minimal separation force by orienting the injector angularly relative to the insertion set to permit free slide out passage of the hub through the oval rim opening.

In a further alternative form of the invention, the plunger head is shaped to define a laterally open undercut slot sized for relatively free slide-fit reception of the needle hub of the insertion set. In this version, the insertion set is assembled quickly and easily with the plunger head of the injector by laterally sliding the hub into the laterally open slot, thereby orienting the medical needle generally coaxially relative to the central axis of the injector barrel and plunger head. In this position, the plunger head can be retracted and locked, followed by appropriate trigger member release for transcutaneously placing the medical insertion needle. After the needle is placed on the patient, the injector can be disassembled from the insertion set by laterally sliding the injector relative to the needle hub. Alternatively, the injector can be withdrawn or retracted from the patient's skin to slidably separate the needle from the insertion set which remains in place on the patient's skin.

Other features and advantages of the present invention will become more apparent from the following detailed description, taken in conjunction with the accompanying drawings which illustrate, by way of example, the principle of the invention.

BRIEF DESCRIPTION OF THE DRAWINGS

The accompanying drawings illustrate the invention. In such drawings:

FIG. 4 is an enlarged exploded perspective view illustrating assembly of the injector with a subcutaneous insertion set;

FIG. 6 is a transverse sectional view taken generally on the line 6—6 of FIG. 5;

FIG. 7 is an enlarged longitudinal sectional view taken generally on the line 7—7 of FIG. 2;

FIG. 8 is an enlarged and exploded fragmented perspective view illustrating a trigger assembly for use in the injector;

FIG. 9 is a longitudinal sectional view similar to FIG. 5, and showing the injector with insertion set received therein for transcutaneous placement through the skin of a patient;

FIG. 10 is a transverse sectional view taken generally on the line 10—10 of FIG. 9;

FIG. 11 is a longitudinal sectional view taken generally on the line 11—11 of FIG. 9;

FIG. 12 is a rear end elevation view taken generally on the line 12—12 of FIG. 11, and depicting the trigger assembly in a locked position;

FIG. 14 is a rear end elevation view taken generally on the line 14—14 of FIG. 13, similar to FIG. 12, but showing the trigger assembly in an unlocked position;

FIG. 17 is a perspective view depicting an alternative preferred form of the invention;

FIG. 18 is a front elevation view of the injector shown in FIG. 17;

FIG. 19 is a front or nose end view of the injector, taken generally on the line 19—19 of FIG. 18;

FIG. 20 is an enlarged side elevation view of the injector, taken generally on the line 20—20 of FIG. 19;

FIG. 21 is a further enlarged longitudinal sectional view taken generally on the line 21—21 of FIG. 17;

FIG. 22 is an enlarged exploded perspective view illustrating construction details of a plunger and trigger member for use in the injector of FIG. 17;

FIG. 23 is an enlarged longitudinal sectional view similar to FIG. 21, and depicting the injector with the trigger member in a cocked position;

FIG. 24 is a fragmented perspective view showing the upper end of the injector depicted in FIG. 23, with the trigger member in the cocked position;

FIG. 25 is an enlarged and fragmented longitudinal sectional view illustrating actuation of the trigger member;

FIG. 26 is an enlarged and fragmented longitudinal sectional view showing the plunger in a fully advanced position with the insertion set placed on the patient's skin;

FIG. 27 is an enlarged fragmented longitudinal sectional view taken generally on the line 27—27 of FIG. 22, and depicting a portion of the plunger;

FIG. 28 is a front or nose end elevational view of the plunger, taken generally on the line 28—28 of FIG. 27;

FIG. 29 is an enlarged fragmented longitudinal sectional view illustrating release of the injector from an insertion set placed on the patient's skin;

FIG. 30 is an exploded perspective view generally similar to FIG. 17, but depicting a further alternative preferred form of the invention, and showing assembly of an insertion set with the illustrative injector;

FIG. 31 is a perspective view similar to FIG. 32, depicting further assembly of the insertion set with the injector;

FIG. 32 is an enlarged fragmented vertical sectional view taken generally on the line 32—32 of FIG. 31;

DETAILED DESCRIPTION OF THE PREFERRED EMBODIMENTS

Figure 1:
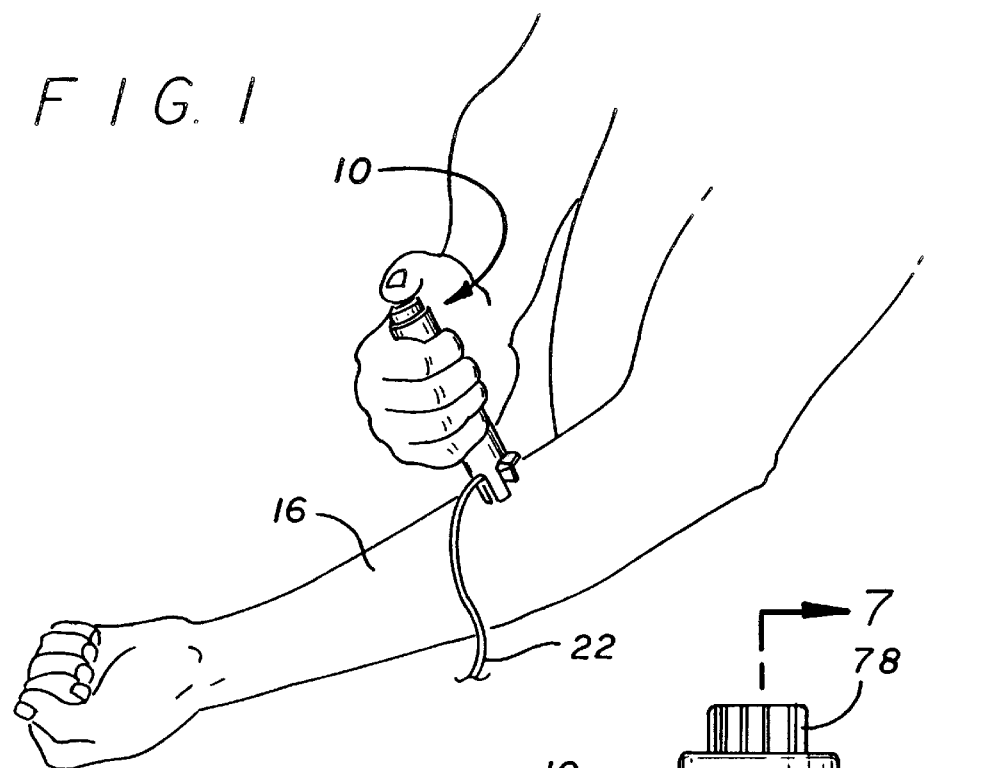
FIG. 1 is a perspective view illustrating use of an automatic injector embodying the novel features of the invention.
Figure 3:
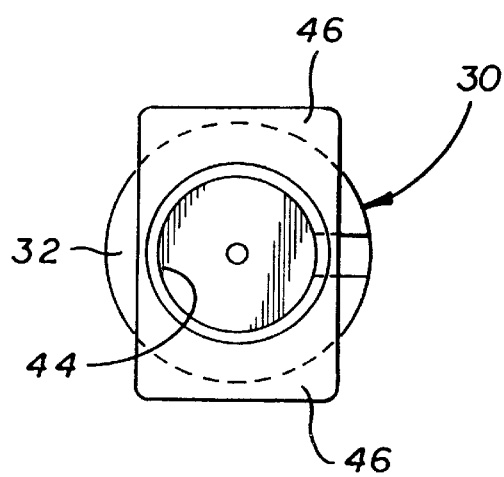
FIG. 3 is a front or nose end view of the injector, taken generally on the line 3—3 of FIG. 2.
Figure 2:
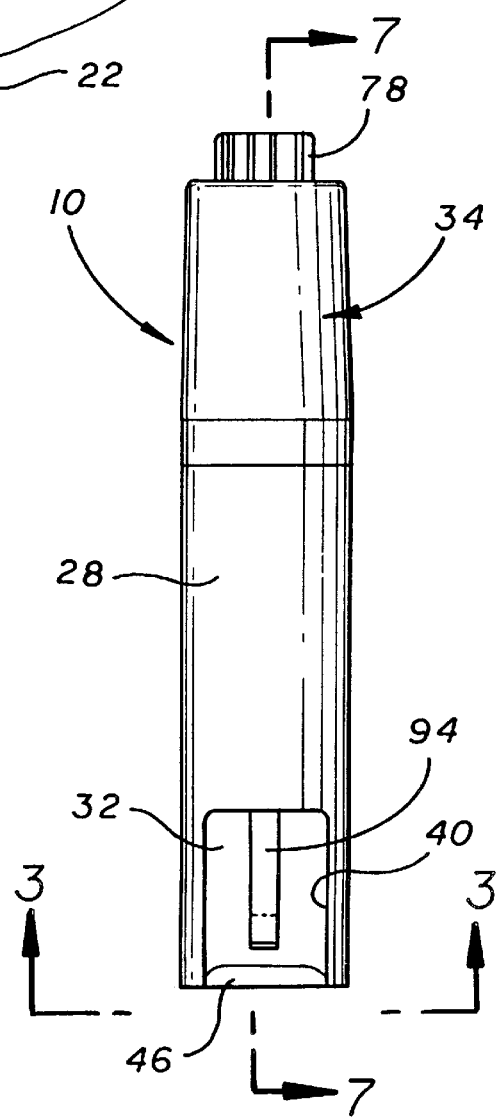
FIG. 2 is an enlarged front elevation view of the injector shown in FIG. 1.

As shown in the exemplary drawings, an injector referred to generally by the reference numeral 10 is provided for quick and easy transcutaneous placement of a medical needle, particularly such as an insertion needle 12 of the type provided with a subcutaneous insertion set 14 as depicted in FIGS. 4 and 7. The injector 10 includes a trigger-type actuator mechanism for transcutaneous placement of the insertion needle 12 with a controlled speed and force, and with the insertion needle 12 oriented at a desired angular position relative to the skin 16 (FIGS. 1 and 9) of the patient.

The automatic injector 10 of the present invention, as shown in the illustrative drawings, is particularly designed for placement of the insertion needle 12 of a subcutaneous insertion set 14, such as an insertion set of the general type shown and described in U.S. Pat. Nos. 4,755,173; 5,176,662; and 5,257,980, which are incorporated by reference herein. Such insertion sets 14 are used to infuse medical fluids such as selected medications to a patient, with one example being the administration of insulin to a diabetic by operation of a programmable medication infusion pump (not shown) of the type described in U.S. Pat. No. 4,685,903. Alternatively, the injector 10 may be used to transcutaneously place a medical needle associated with other types of insertion sets, such as transcutaneous sensor insertion sets of the general type shown and described in U.S. Pat. Nos. 5,390,671; 5,560,806; and 5,586,553, which are also incorporated by reference herein. Such insertion sets are used, for example, to subcutaneously place a biological sensor such as a glucose sensor for monitoring patient glucose levels.

As shown best in FIG. 4 with respect to an insertion set 14 for infusing medical fluids to a patient, the insertion needle 12 is connected to a hub 18 at a rear or proximal end thereof, and protrudes through a housing 20 of the insertion set 14, wherein the housing 20 defines an internal chamber (not shown) for receiving medication via infusion tubing 22. An enlarged base, typically in the form of resilient or flexible wings 24, is provided on the housing 20 for stable affixation to the skin 16 of a patient. The insertion needle 12 protrudes downwardly through the housing 20 and the winged base 24 to extend through a soft and flexible cannula 26. The insertion needle 12 is provided for transcutaneous placement of the cannula 26, after which the insertion needle is retracted from the set 14 (FIG. 16) to permit medication delivery through the cannula 26 to the patient.

The injector 10 of the present invention represents a simple device which can be used by the patient to quickly and easily place the subcutaneous insertion set 14 in a proper transcutaneous position and orientation, at a selected insertion site. The injector 10 is designed to project the insertion set toward the patient's skin 16 at a controlled force and speed for quickly piercing the skin in a manner insuring proper placement of the insertion needle 12 and cannula 26, while minimizing patient anxiety and/or discomfort. Improper and/or partial placement of the insertion needle 12 is thus avoided.

In general terms, as shown in one preferred form is FIGS. 1–5, the injector 10 comprises a cylindrical forward barrel 28 having a plunger 30 mounted therein for longitudinal sliding movement within a hollow bore between a forward advanced position (FIG. 5) and a rearward retracted position (FIG. 9). The plunger 30 has a head 32 at a forward end thereof shaped for releasibly receiving and retaining the subcutaneous insertion set 14, in a manner to be described in more detail. A rear end of the plunger 30 cooperates with a trigger-type actuator assembly 34 mounted on the rear end of the barrel 28. The trigger actuator assembly 34 is adapted to hold the plunger 30 in a retracted position, against the force of a compressed drive spring 36. A trigger button 38 of the actuator assembly 34 is adapted for fingertip depression to release the plunger 30 for spring-loaded travel toward the advanced position, and corresponding transcutaneous placement of the insertion needle 12 through the patient's skin.

FIGS. 2–5 illustrate construction details of the injector barrel 28, wherein the forward or nose end thereof defines a flat and generally planar surface for placement against the skin of a patient (FIG. 1) with a longitudinal axis of the barrel 28 oriented generally perpendicular to the patient's skin 16. The barrel 28 has a size and shape for substantially mated sliding fit reception of the insertion set 14, with the insertion needle 12 and related cannula 26 projecting in a direction for placement on a patient. In this regard, the nose end of the barrel 28 defines an opposed pair of relatively wide and open-ended cut outs 40 for slide-fit reception of the oppositely projecting base wings 24. A narrower slot 42 is also formed in the barrel nose end, at a location for slide-fit reception of the infusion tubing 22 attached to the infusion set 14. In the case of a transcutaneous sensor insertion set, the slot 12 accommodates slide-fit reception of a coupling element such as the proximal end of a flexible sensor, or a conductor associated therewith for convenient coupling of a subcutaneously placed sensor with an external monitoring device (not shown). Thus, the forward or nose end of the barrel 28 accommodates mated sliding reception of the subcutaneous insertion set 14 therein for movement along the cut outs 40 and the slot 42 between the advanced position (FIG. 5) disposed substantially at the forwardmost end of the barrel 28, and the retracted position (FIG. 9) with the base wings 24 and infusion tubing 22 positioned substantially at the inboard ends of the cut outs 40 and the associated slot 42.

The plunger 30 includes the head 32 of generally cylindrical shape for slide-fit reception within the injector barrel 28. A forward end of the head 32 includes a cylindrical counterbore recess 44 for receiving the hub 18 and housing 20 of the insertion set 14, with the enlarged base wings 24 fitted against a pair of outwardly protruding backstop flanges 46 adapted for slide-fit reception within the cut outs 40 in the barrel nose end. A pair of track arms 48 (FIG. 5) protrude rearwardly from the plunger head 32 and include out-turned latch fingers 50 for guided reception within longitudinally extending track slots 52 formed in the barrel 28 at a location spaced aft from the barrel nose end. These track arms 48 thus cooperate with the barrel track slots 52 to guide the plunger 30 between the advanced position (FIGS. 5 and 7) and the retracted position (FIG. 9).

The plunger 30 also includes a central drive stem 54 (FIG. 5) which protrudes rearwardly from the plunger head 32 within the barrel interior. The rearward end of the drive stem 54 is longitudinally split to define a pair of trigger arms 56 which have out-turned trigger fingers 58 on the rearward ends thereof.

Figure 5:
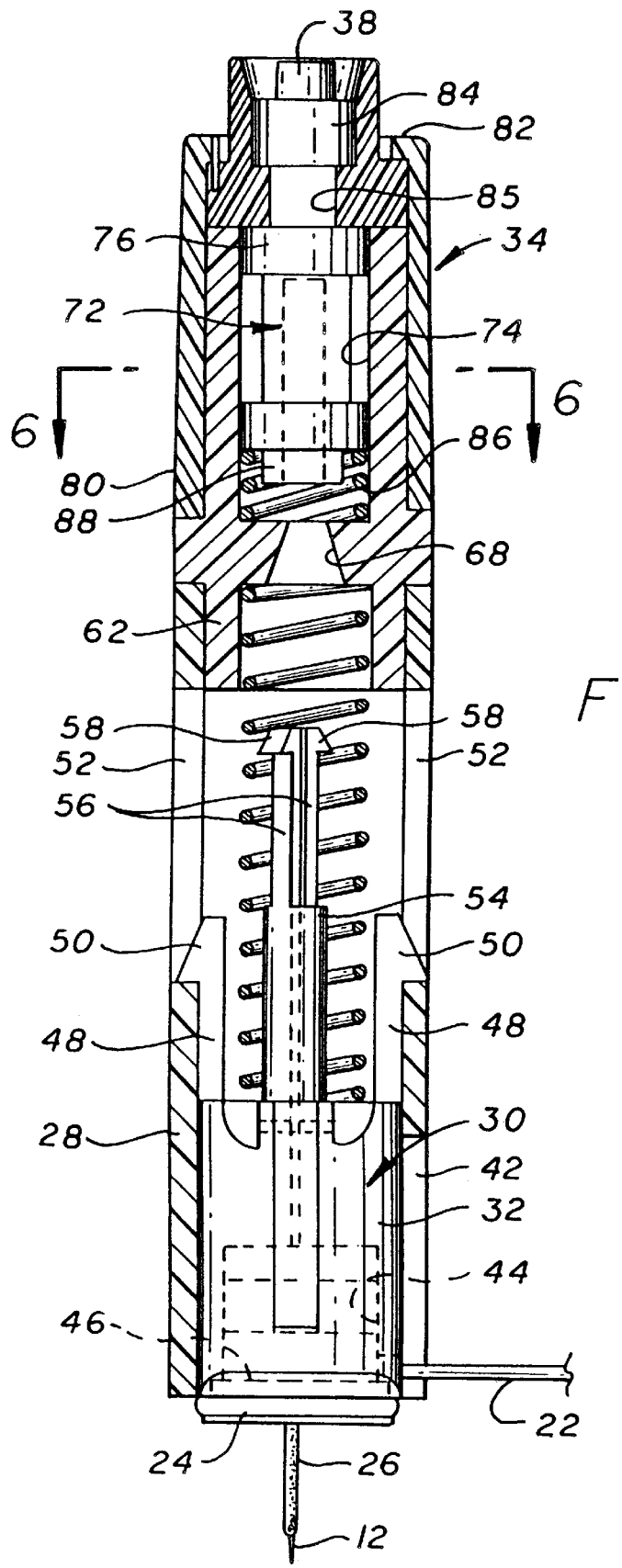
FIG. 5 is a further enlarged longitudinal sectional view taken generally on the line 5—5 of FIG. 4.

The trigger-type actuator assembly 34 is mounted on the rearward end of the injector barrel 28, and generally functions to releasibly retain the plunger 30 in a retracted and cocked position, ready for rapid and spring-loaded actuation upon depression of the trigger button 38 to place the insertion set 14 on the patient. More particularly, as shown best in FIGS. 5–9, the trigger assembly 34 comprises a main support cap 60 having a mounting sleeve 62 protruding in a press-fit and preferably adhesively connected manner into the rear or aft end of the injector barrel 28. The drive spring 36 comprises a coil spring positioned about the drive stem 54 on the plunger 30 and reacts between a rearward face 64 of the plunger head 32, and a shoulder 66 on the support cap 60. The drive spring 36 normally biases the plunger 30 toward the advanced position (FIGS. 5 and 7). However, an insertion set 14 seated in the plunger head 32 can be pressed rearwardly against the plunger 30 to move the plunger to the retracted position, as viewed in FIG. 9, with the trigger fingers 58 passed through a conical or tapered latch bore 68 formed in the support cap 60 to engage a shoulder 70 on an opposite side of the support cap 60. In this regard, the trigger fingers 58 have ramped outboard faces to accommodate movement of the fingers 58 radially toward each other as they pass through the latch bore 68. When the trigger fingers 58 pass entirely through the bore 68, the spring resilience of the trigger arms 56 is sufficient to spread the trigger fingers 58 so that they engage the shoulder 70. In this retracted plunger position, the drive spring 36 is retained in a compressed and cocked condition, with the insertion set 14 including the insertion needle 12 and related cannula 26 withdrawn into the interior of the barrel 28, in spaced relation to the patient's skin 16.

The trigger actuator assembly 34 additionally includes an actuator pin 72 mounted within a noncircular bore 74 (FIGS. 6 and 7) formed in the support cap 60 for longitudinal sliding movement through a short stroke, relative to the plunger 30. In this regard, the actuator pin 72 includes one or more noncircular lands 76 for slide-fit reception within the bore 74, to prevent actuator pin rotation therein. The actuator pin 72 is held within the bore 74 by a stepped lock ring 78 which is retained against a rearward end of the support cap 60 by a press-fit outer retainer sleeve 80 having an inturned rim 82 at the rearward end thereof. Importantly, as shown best in FIG. 8, an oblong land 84 is formed on the actuator pin 72 for mated slide-fit reception through an oblong recess 85 formed in the lock ring 78. A return spring 86 (FIG. 7) is carried within the support cap bore 74 and reacts between the shoulder 70 and a nose end of the actuator pin 80 for biasing the actuator pin 80 rearwardly within the support cap.

Figure 13:
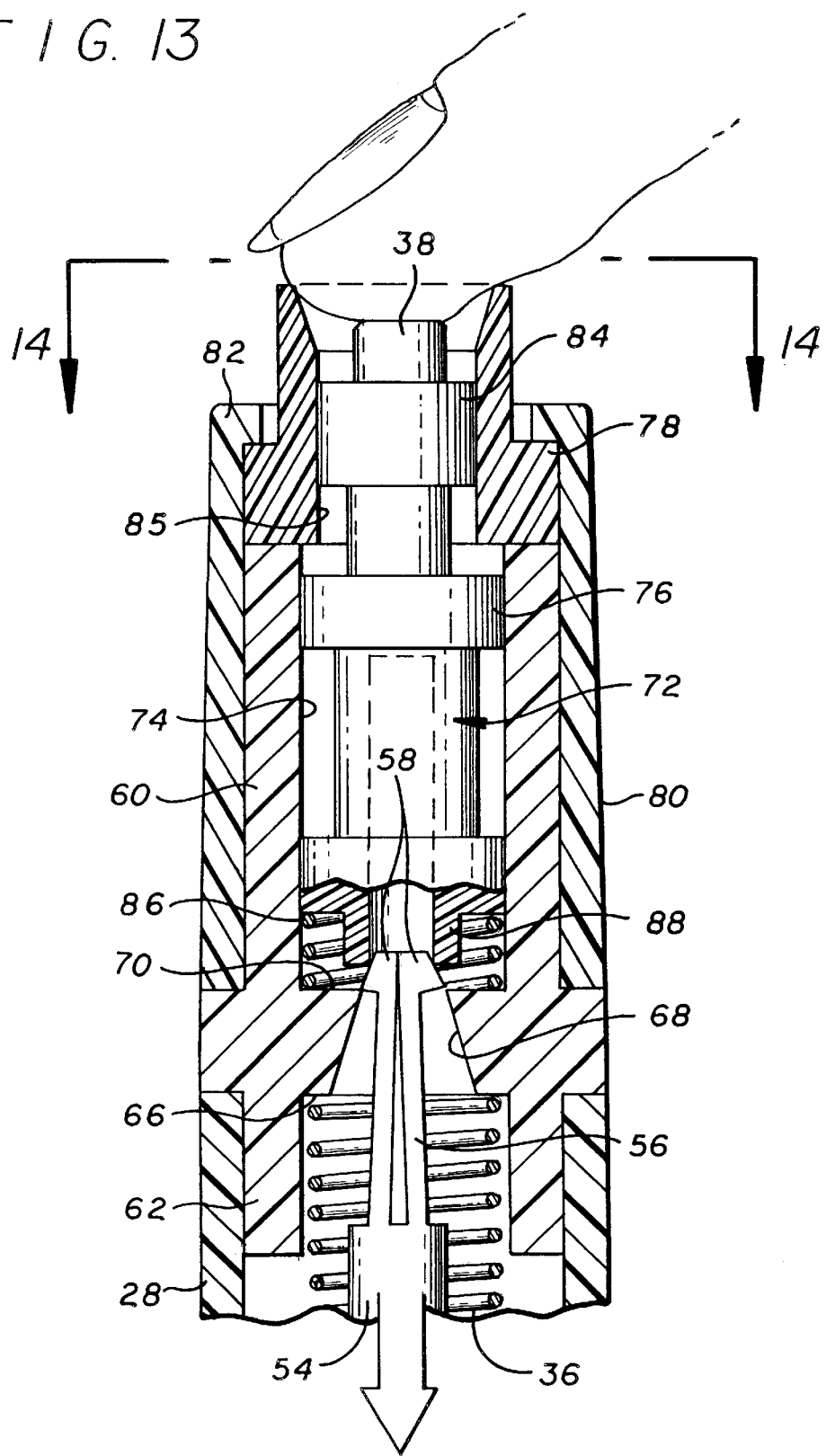
FIG. 13 is an enlarged fragmented longitudinal view similar to a portion of FIG. 11, but depicting actuation of the trigger assembly for releasing the spring-loaded plunger.
Figure 15:
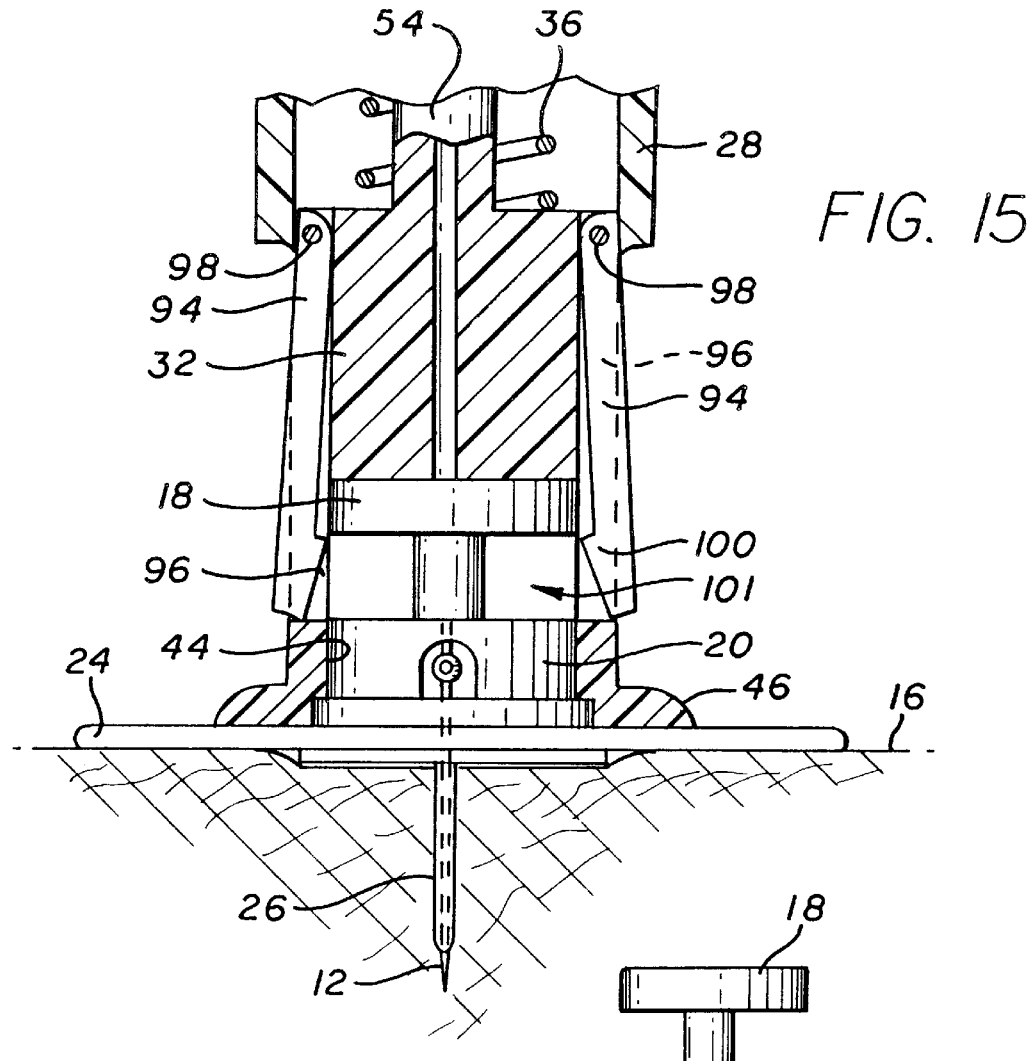
FIG. 15 is a fragmented longitudinal sectional view depicting the spring-loaded plunger in a fully advanced position with the insertion set placed on the patient's skin.

The rearmost end of the actuator pin 72 defines the trigger button 38. As shown in FIGS. 11 and 13, the trigger button 38 can be depressed with a fingertip to move the actuator pin 72 through a short stroke against the return spring 86 in a direction toward the trigger fingers 58 at the rear end of the plunger 30. As shown best in FIG. 13, the actuator pin 72 has a hollowed cylindrical forward tip 88 with a diametric size for engaging and squeezing the trigger fingers 58 together at the rear end of the plunger 30, in a manner enabling those trigger fingers 58 to pass back through the tapered conical latch bore 68. As soon as the trigger fingers 58 thus release from engagement with the shoulder 70 on the support cap 60, the drive spring 36 translates the plunger 30 with the insertion set 14 thereon with a rapid and controlled force and speed toward the advanced position, resulting in transcutaneous placement of the needle 12 and cannula 26, as viewed in FIG. 15. Importantly, the spring rate characteristics of the drive spring 36 and the distance of plunger stroke are chosen for a substantially optimized and proper transcutaneous placement of the needle 12 and cannula 26, all in a manner which minimizes patient discomfort during the needle placement procedure. Moreover, by forming the nose end of the injector barrel 28 with a squared-off shape as shown, the injector 10 can be easily oriented substantially perpendicular to the skin 16 for proper placement of the insertion set.

Depression of the actuator pin 72 by means of the trigger button 38 requires the lock ring 78 to be rotatably oriented in a position aligning the oblong recess 85 therein with the oblong land 84 on the actuator pin. Accordingly, when these oblong structures are rotationally aligned (FIGS. 13–14), the injector 10 is armed for trigger button depression and corresponding release of the retracted and cocked plunger. However, the lock ring 78 can be rotated relative to the actuator pin 72 to misalign these oblong structures, as shown in FIGS. 9–12, whereupon the actuator pin 72 is locked in a rearward position against depression and actuation. A set pin 90 on the lock ring 78 may be provided and received within an arcuate notch 92 formed in the retainer sleeve flange rim 82, to permit lock ring rotation back-and-forth through a part circle increment, on the order of about 90 degrees. Appropriate indicia may be applied to the retainer sleeve rim 82, such as the letter "L" for "locked" and the letter "A" for "armed", as viewed in FIGS. 12 and 14, to provide a visual indication of the setting of the trigger assembly 34.

In accordance with one aspect of the invention, the plunger head 32 additionally includes a safety lock mechanism in the form of a pair of safety lock arms 94 pivotally carried in narrow slots 96 formed in the plunger head 32. These safety lock arms 94 have rearward ends connected to the head 30 by pivot pins 98, and forward ends defining contoured lock fingers 100 which protrude into the plunger head recess 44. As shown in FIG. 7, the safety lock arms 94 and their associated lock fingers 100 have a size and shape so that the fingers 100 can engage and retain the hub 18 of the insertion set 14, for example, by fitting into a recess 101 defined between the hub 18 and housing 20 of the insertion set. Importantly, the locations of the lock arm pivot points are chosen to insure that the lock arms 94 engage and retain the insertion set 14 whenever the plunger 30 is moved from the advanced position (FIG. 7) toward and to the retracted position (FIG. 9). When the plunger 30 reaches the fully advanced position, the safety lock arms 94 including their respective pivot pins 98 are disposed within the wide cut outs 40 and are therefore free to swing outwardly, relative to the insertion set 14, to accommodate separation of the insertion set from the injector 10 with a substantially minimum separation force. This configuration has been found to be highly effective as a safeguard to prevent the insertion set 14 from being thrown as a projectile from the injector 10, in the event that the trigger assembly 34 is activated without prior placement of the injector 10 firmly against the patient's skin 16.

In use, the subcutaneous insertion set 14 can be placed quickly and easily into the open nose end of the injector barrel 28, within the recess 44 formed in the plunger head 32. Such assembly of the insertion set 14 with the injector 10 requires simple alignment of the base wings 24 and infusion tubing 22 with the appropriate cut outs and slots 40, 42 formed in the nose end of the barrel 28. The insertion set 14 and plunger 30 can then be manually retracted rearwardly, against the drive spring 36, to the retracted position with the plunger 30 cocked and latched as viewed in FIGS. 9 and 11. The injector 10 can then be placed firmly against the patient's skin 16, with the insertion set 14 supported in the proper orientation and at a predetermined distance from the skin 16. Simple depression of the trigger button 38 releases the cocked plunger 30 for spring-loaded travel rapidly albeit with a controlled speed and force of insertion, to ensure penetration of the patient's skin with minimal discomfort, and in a manner which properly places the insertion needle and cannula. The safety lock arms 94 prevent accidental projection of the insertion set 14 through free space, in the event that the trigger button 38 is prematurely depressed. When the insertion set 14 is properly placed, however, the safety lock arms 94 release from the insertion set with minimal force, for easy separation of the injector 10 from the insertion set 14.

Figure 16:
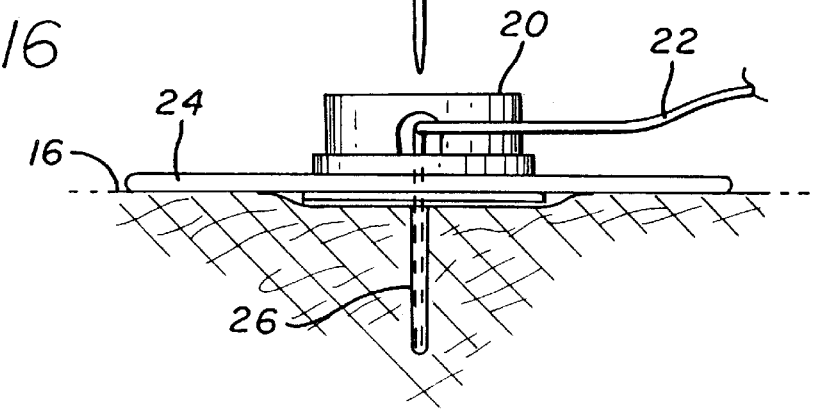
FIG. 16 is an exploded perspective view illustrating separation of the insertion needle from the cannula of the subcutaneous insertion set.
Figure 33:
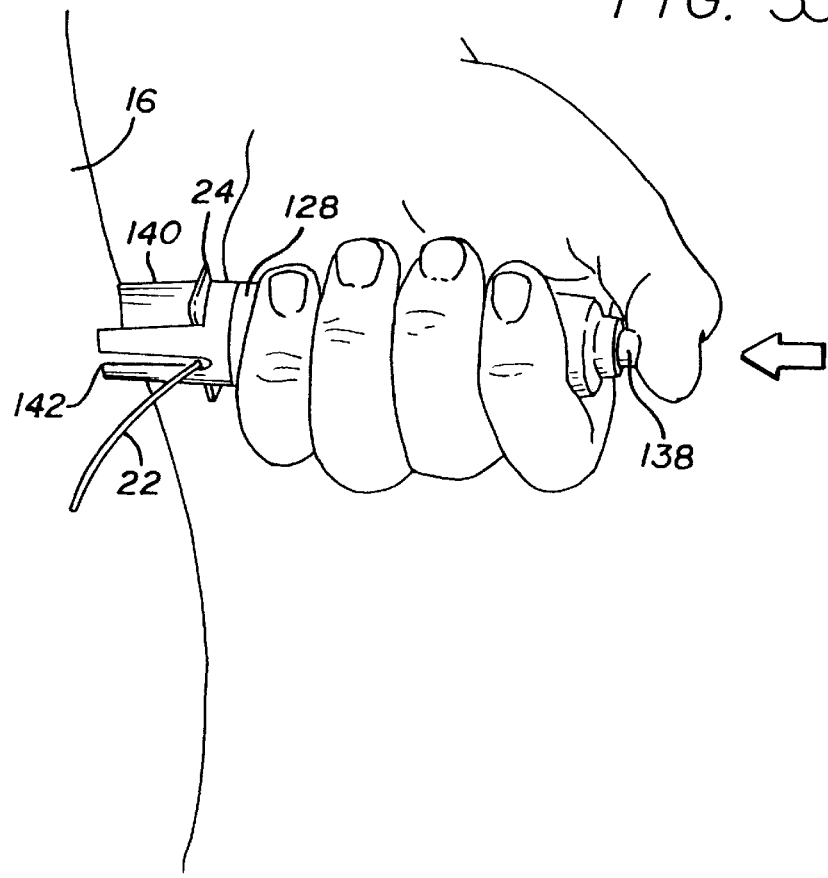
FIG. 33 is a perspective view showing use of the injector of FIGS. 30–32 for transcutaneous placement of the insertion set.
Figure 34:
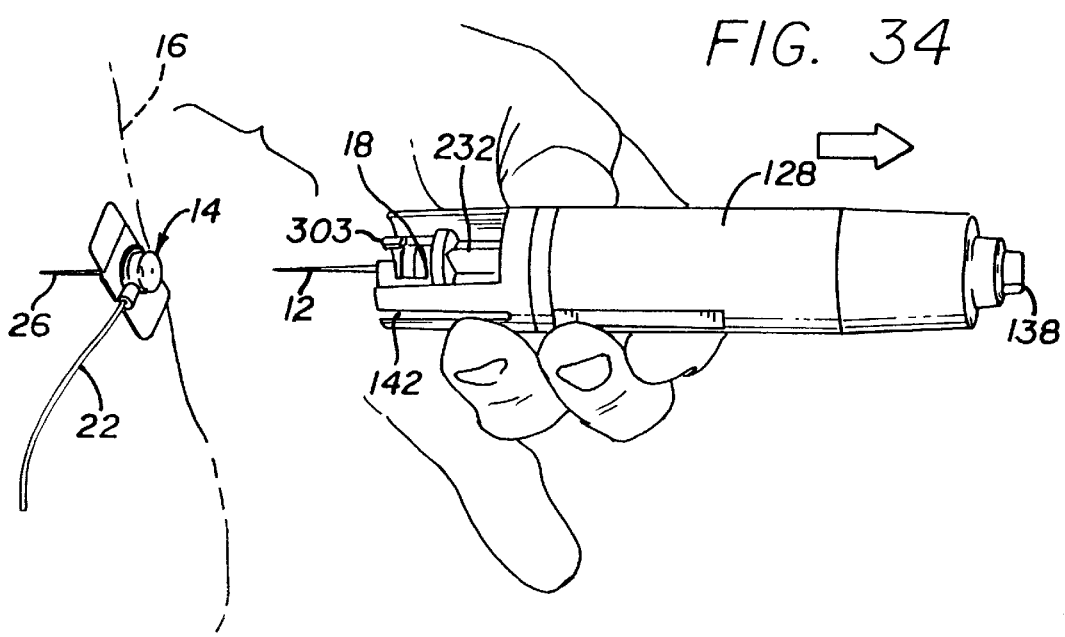
FIG. 34 is an exploded perspective view similar to FIG. 33, and showing use of the injector to separate a medical needle from the installed insertion set.

Following separation of the injector 10 from the placed insertion set 14, the insertion needle 12 can be withdrawn quickly and easily from the cannula as viewed in FIG. 16. Thereafter, the insertion set 14 can be used in a normal manner to deliver a selected medication through the infusion tubing 22 and cannula 26 to the patient.

An alternative preferred form of the invention is shown in FIGS. 17–29, wherein components corresponding in structure and function to those described previously with respect to FIGS. 1–16 are identified by common reference numerals increased by 100. The embodiment of FIGS. 17–29 show a modified injector 110 constructed from a reduced number of parts and including an alternative safety lock mechanism for preventing undesired projection of the insertion set 14 through free space in the event of injector operation without placing the nose end thereof firmly against the skin 16 of a patient. However, the alternative safety lock mechanism again permits quick and easy separation of the injector 110 from the insertion set 14, with minimal separation force. Once again, although an insertion set for infusing medical fluids to a patient will be shown and described, it will be understood that alternative insertion sets such as transcutaneous sensor insertion sets and the like as previously referenced herein may be used with the injector 110.

In general, the modified injector 110 comprises a plunger 130 and a trigger-type actuator 134 assembled with a generally cylindrical hollow barrel 128. The plunger 130 has a generally cylindrical plunger head 132 which defines a counterbore recess 144 for receiving and retaining the hub 18 of the insertion set 14. As shown best in FIGS. 27–29, a radially inwardly projecting rim 202 is formed on the plunger head 132 generally at a leading or nose end of the recess 144, wherein this rim 202 has a noncircular and preferably oval or elliptical shape (FIG. 28) to accommodate reception of the hub 18 into the recess 144 provided that the hub 18 is oriented angularly relative to a central longitudinal axis of the plunger 130 and barrel 128. Similar angular orientation of these components accommodates quick and easy separation thereof. However, when the insertion set 14 is oriented with the medical needle 12 aligned coaxially with the barrel center axis, a portion of the rim 202 projects into the insertion set recess 101 to prevent release of the insertion set 14 from the injector 110.

More specifically, with reference to FIGS. 17–20, the barrel 128 again has a forward or nose end defining a flat and generally planar surface for firm placement against the skin of a patient. The nose end of the barrel 128 has a pair of relatively wide and generally opposed cut outs 140 formed therein for slide-fit reception of the base wings 24 of the insertion set 14, in combination with a narrower slot 142 for slide-fit reception of the infusion tubing 22. This slot 142 may be formed in one or both sides of the barrel nose end.

The plunger 130 is slidably fitted into the barrel 128 for movement between an advanced position shown in FIGS. 17, 18, 20 and 21, and a retracted position shown in FIG. 23. The plunger 130 includes the modified plunger head 132 of generally cylindrical shape, formed preferably to include a shallow notch or groove 133 in one side thereof for slide-fit reception of the infusion tubing 22 on the insertion set 14. In this regard, the plunger head groove 133 is formed in a position aligned with the narrow slot 142 in the nose end of the barrel.

The plunger head 132 is formed integrally with a drive stem 154 which projects rearwardly within the barrel interior. As shown best in FIG. 22, the drive stem 154 is flanked by and formed integrally with a pair of rearwardly projecting track arms 148 which have latch fingers 150 formed at the rear ends thereof. As shown in FIGS. 21 and 23, these latch fingers 150 are received slidably within longitudinally extending track slots 152 formed in the barrel 128, and function to guide the plunger 130 between the advanced and retracted positions. Cushioning material (not shown) may be included at the leading ends of the track slots 152 to form a combined stop upon spring driver advancing motion of the plunger 130, as will be described.

The plunger 130 additionally includes a pair of trigger arms 156 which project generally rearwardly from a rear end of the drive stem 154 and have out-turned trigger fingers 158 at the rear ends thereof (FIG. 22). These trigger fingers 158 are adapted and sized for partial radial compression toward each other as they ride within the barrel base when the plunger 130 is displaced from the advanced position (FIG. 21) to the retracted position (FIG. 23). As the retracted position is reached, the trigger fingers 158 are spring-loaded by the resiliency of the trigger arms 156 to move outwardly for partial reception into relatively short trigger slots 159 formed in the barrel 128. In this position, as shown in FIG. 23, the triggers fingers 158 retain the plunger 130 in the retracted position.

A drive spring 136 is mounted within the barrel 128 to react between the trigger-type actuator 134 and the plunger 130, in the same manner as previously described with respect to FIGS. 1–16. In this regard, the trigger actuator 134 comprises a generally cylindrical actuator sleeve 188 mounted slidably within the barrel 128 at the rear or upper end thereof. This actuator sleeve 188 has a tapered or ramped leading edge face 188' (FIGS. 22, 23 and 25) for engaging matingly shaped ramped outer faces of the trigger fingers 158, to radially compress the trigger arms 156 and release the plunger 130 for spring-loaded travel from the retracted and cocked position to the advanced position. A trigger button 138 is formed integrally with the actuator sleeve 188 and is exposed for fingertip depression at the rear or top of the barrel 128 to move the actuator sleeve 188 into releasing engagement with the trigger fingers 158.

As shown best in FIGS. 22 and 24–26, the triggers button 138 extends through an opening formed in the rear of the barrel 128, generally within a lock sleeve 178 formed integrally with the barrel 128. The lock sleeve 178 defines an oppositely formed pair of guide slots 192 for aligned reception of a pair of outwardly radiating lock tabs 184 formed on the trigger button 138. When the tabs 184 are rotationally aligned with the guide slots 192, the trigger button 138 can be depressed to actuate the spring-locked plunger, as described. However, the lock tabs 184 have sufficient length to permit fingertip rotation of the actuator 134 to re-position the tabs 184 within shallow lock grooves 193 formed adjacent the guide slots 192. When the tabs 184 are seated in the lock grooves 193, the lock sleeve 178 blocks depression of the triggers button 138 and thereby locks the injector 110 against actuation. Return rotation of the actuation 134 to re-align the tabs 184 with the guide slots 192 is required before the injector can be activated.

In accordance with one aspect of the invention, the plunger head 132 includes the safety lock mechanism in the form of the noncircular rim 202 at the leading end of the recess 144 in the plunger head. As shown in FIGS. 27 and 28, the rim 202 has a generally elliptical shape defining a major axis that is greater than the diameter of the hub 18 on the insertion set 14, and a minor axis that is less than the hub diameter. With this geometry, and by providing sufficient axial depth to the plunger head recess 144, the hub 18 can be fitted into the plunger head by angularly orienting the components to permit slide-fit of the hub 18 through the major axis portion of the rim 202. Subsequent re-orientation of the components to align the medical needle 12 generally coaxially with plunger head 132 enables the minor axis portion of the rim 202 to project into the insertion set recess 101, thereby locking the components together. Thereafter, when the insertion set 14 is placed on the patient (FIG. 29), the components are easily separated by lifting the injector 110 off the infusion set 14 at the same angle to allow the hub 18 to press freely through the major axis center of the rim 202. Importantly, such engagement and disengagement of the components occurs with essentially no resistance force to separation. The insertion set 14 can be oriented angularly relative to the plunger 130 only when the plunger is in the advanced position, with the adjacent barrel 128 precluding such angular orientation when the plunger 130 is moved rearwardly from the restricted position.

In an alternative mode of operation, subsequent to actuation of the injector 110 to place the insertion set 14 or the patient, the injector 110 can be simply withdrawn or retracted in a direction away from the patient's skin 16, in which case the rim 202 at the nose end of the plunger head 132 will engage the needle hub 18 and thereby gently withdraw the medical needle 12 from the insertion set 14. In this manner, the needle 12 is retracted from the cannula 26 which remains at the desired transcutaneous insertion site.

A further alternative preferred form of the invention is shown in FIGS. 30–34, wherein a further modified injector 210 is constructed and operated generally as shown and described in FIGS. 17–29, but wherein an alternative configuration for a plunger head 232 is provided. FIGS. 30–32 show the injector 210 with the plunger head 232 in the advanced position within the front or nose end of the barrel 128 which includes the wide cut outs 140 and the narrow slot 142 for respective slide-fit reception of the base wings 24 and the tubing 22 of the insertion set 14. As shown, the modified plunger head 232 has a laterally open recess 244 formed therein of undercut geometry and laterally exposed through the cut outs 140 when the plunger is in the advanced position. The insertion set 14 can be slide-fit assembled with the plunger head 232, by fitting the hub 18 into the wider upper region of the recess 144, with an inturned rim 302 at the leading end of the plunger head fitting into the insertion set recess 101. A laterally open gap 303 (FIG. 34) in the rim 302 permits slide-fit reception of the hub 18 into the recess 244, and a short carrier post 304 (FIG. 32) may be provided at the base of the recess 244 to seat within a shallow detent in the top of the hub.

With the insertion set 14 assembled with the plunger head 232, as viewed in FIG. 32, the plunger can be retracted and cocked as previously shown and described with respect to FIGS. 17–29. The cut outs 140 and slot 142 accommodate sliding movement of the insertion set 14 with the plunger head 232 during such retraction. Thereafter, the front or nose end of the injector 210 can be placed firmly against the patient's skin (FIG. 33) and the trigger button 138 depressed to release the plunger so that the medical needle 12 is transcutaneously placed with the controlled drive force and speed. During forward drive motion of the plunger, the forward rim 302 on the plunger head 232 prevents projectile release of the insertion set. After placement of the insertion set on the patient, the injector 210 can be laterally displaced relative to the insertion set for quick and easy separation therefrom. Alternately, as viewed in FIG. 34, the injector 210 can be withdrawn or retracted from the insertion set 14 to slidably withdraw the medical needle 12 while leaving the insertion set in place on the patient.

A variety of further modifications and improvements to the automatic injector unit of the present invention will be apparent to persons skilled in the art. Accordingly, no limitation on the invention is intended by way of the foregoing description and accompanying drawings, except as set forth in the appended claims.

What is claimed is:

1. An injector for transcutaneously placing an insertion needle of a subcutaneous insertion set through the skin of a patient, comprising:

a barrel having an elongated base formed therein;

a plunger slidably received within the bore for movement between an advanced position and a retracted position, the plunger including a support structure for receiving and supporting the insertion set in a position with the insertion needle oriented for transcutaneous placement upon movement of the plunger from the retracted position to the advanced position, wherein the plunger is substantially incapable of delivering a fluid from the insertion set upon movement from the retracted position to the advanced position; and a drive for urging the plunger with a controlled force and speed from the retracted position toward the advanced position to transcutaneously place the insertion needle, wherein the support structure is removable from the insertion set while maintaining the transcutaneous placement of the insertion needle.

2. The injector of claim 1, wherein the barrel has a forward end defining a generally planar surface for placement against the skin of a patient with the barrel in a predetermined orientation relative to the patient's skin.

3. The injector of claim 2, wherein the plunger and the insertion needle supported thereby are substantially retracted within the bore when the plunger is in the retracted position, the barrel having at least one slot formed therein and extending longitudinally from the forward end thereof.

4. The injector of claim 2, wherein the insertion set comprises at least one outwardly radiating base wing for securing the insertion set to the patient's skin, and at least one outwardly radiating coupling element, the barrel having at least one cut out and at least one slot formed therein to extend longitudinally from the forward end thereof for respective slide-fit reception of the base wing and coupling element.

5. The injector of claim 1, further including a trigger for actuating the drive.

6. The injector of claim 5, wherein the trigger includes a trigger actuator for fingertip depression to actuate the drive for movement of the plunger from the retracted position to the advanced position.

7. The injector of claim 6, wherein the drive comprises spring means for spring-loaded movement of the plunger from the retracted position to the advanced position.

8. The injector of claim 5, wherein the trigger includes lock means for releasibly locking the plunger in the retracted position.

9. The injector of claim 1, wherein the barrel and the plunger include cooperatively engageable track means for guiding movement of the plunger between the advanced and retracted positions while retaining the plunger against rotation relative to the barrel.

10. The injector of claim 1, wherein the insertion needle is provided as part of an insertion set, and further wherein the plunger comprises a plunger head having a recess formed therein for mated slide-fit reception of at least a portion of the insertion set.

11. The injector of claim 10, wherein the plunger head recess comprises a laterally open undercut recess.

12. The injector of claim 10, wherein the plunger head further includes safety retainer means for retaining the insertion needle on the plunger head during movement from the retracted position to the advanced position, the safety retainer means permitting separation of the insertion needle from the plunger head when the plunger head is in the advanced position.

13. The injector of claim 12, wherein the safety retainer means comprising at least one safety lock arm having one end pivotally mounted on the plunger head and an opposite end defining a lock finger for releasably engaging the insertion needle, the barrel retaining said safety lock arm against outward pivoting motion relative to the plunger head recess when the plunger is moved from the advanced position, the safety lock arm being in a position relative to the barrel for permitting outward pivoting movement with respect to the plunger head recess when the plunger is in the advanced position.

14. The injector of claim 13, wherein the at least one safety lock arm comprises a pair of safety lock arms each having one end pivotally mounted on the plunger and an opposite end defining a lock finger for releasably engaging the insertion needle.

15. The injector of claim 14, wherein the barrel has a forward end with a pair of open-ended cut outs formed therein, the safety lock arms being disposed generally within said cut outs when the plunger is in the advanced position.

16. The injector of claim 12, wherein the safety retainer means comprises a radially inwardly projecting rim of noncircular shape formed generally at a leading end of the plunger head, the rim engaging the insertion needle when the needle is generally aligned coaxially within the plunger head and permitting release of the needle when the needle is angularly oriented relative to the plunger head.

17. The injector of claim 16, wherein the rim has a generally elliptical shape.

18. An injector for transcutaneously placing an insertion needle of a subcutaneous insertion set through the skin of a patient, comprising:

a barrel having an elongated bore formed therein;

a plunger slidably received within the bore for movement between an advanced position and a retracted position, the plunger including a support structure for mated slide-fit reception and support of the insertion set in a position with the insertion needle oriented for transcutaneous placement upon movement of said plunger from the retracted position to the advanced position, wherein the plunger is substantially incapable of delivering a fluid from the insertion set upon movement from the retracted position to the advanced position;

a spring for urging said plunger toward the advanced position; and a trigger for releasably retaining the plunger in the retracted position, the trigger being operable to release the plunger for spring-loaded movement with a controlled force and speed toward the advanced position, wherein the support structure is removable from the insertion set while maintaining the transcutaneous placement of the insertion needle.

19. The injector of claim 18, wherein the plunger further including safety retainer means for retaining the insertion set on the advanced position, the safety retainer means permitting the removal of the insertion set from the plunger when the plunger is in the advanced position.

20. The injector of claim 18, wherein the barrel has a forward end defining a generally planar surface of placement against the skin of a patient with the barrel in a predetermined orientation relative to the patient's skin.

21. The injector of claim 18, wherein the barrel and the plunger include cooperatively engageable track means for guiding movement of the barrel and the plunger between the advanced and retracted positions while retaining the barrel and the plunger against rotation relative to the barrel and the plunger.

* * * * *